(12) United States Patent
Baxter et al.

(10) Patent No.: US 7,416,739 B2
(45) Date of Patent: Aug. 26, 2008

(54) COMPOSITION AND PROCESS FOR RETAINING ACTIVE INGREDIENTS

(75) Inventors: Steven M. Baxter, Chalfont, PA (US);
Willie Lau, Lower Gwynedd, PA (US);
Berislav Markovic, Westfield, NJ (US);
Mark E. Rerek, Scotch Plains, NJ (US);
Curtis Schwartz, Ambler, PA (US);
Thomas R. Tepe, King of Prussia, PA (US); Elliott Zucker, Shahola, PA (US)

(73) Assignee: Rohm and Haas Company, Philadelphia, PA (US)

( * ) Notice: Subject to any disclaimer, the term of this patent is extended or adjusted under 35 U.S.C. 154(b) by 353 days.

(21) Appl. No.: 10/179,776

(22) Filed: Jun. 25, 2002

(65) Prior Publication Data

US 2003/0021847 A1   Jan. 30, 2003

Related U.S. Application Data

(60) Provisional application No. 60/302,577, filed on Jul. 2, 2001.

(51) Int. Cl.
*A61K 9/14* (2006.01)
(52) U.S. Cl. ...................................... 424/484
(58) Field of Classification Search ................ 424/484
See application file for complete search history.

(56) References Cited

U.S. PATENT DOCUMENTS

| | | | |
|---|---|---|---|
| 5,306,485 A | 10/1884 | Hartfeldt | |
| 4,172,122 A * | 10/1979 | Kubik et al. | 424/59 |
| 4,552,755 A * | 11/1985 | Randen | 514/772.4 |
| 4,917,883 A | 4/1990 | Strobridge | |
| 5,316,860 A | 5/1994 | Stewart et al. | 428/473 |
| 5,736,125 A | 4/1998 | Morawsky et al. | 424/59 |
| 5,916,544 A | 6/1999 | Liu et al. | |
| 6,040,409 A * | 3/2000 | Lau et al. | 526/328 |
| 2002/0061322 A1 * | 5/2002 | Keenan et al. | 424/401 |
| 2003/0017125 A1 * | 1/2003 | Rollat et al. | 424/70.1 |
| 2003/0022981 A1 | 1/2003 | Baxter et al. | |
| 2003/0022987 A1 * | 1/2003 | Matz et al. | 524/814 |

FOREIGN PATENT DOCUMENTS

| | | |
|---|---|---|
| EP | 0438216 B1 | 3/1998 |
| WO | 94/07463 | 4/1994 |
| WO | WO 96/36308 | 11/1996 |

OTHER PUBLICATIONS

2002 Derwent Information Ltd. Dialog File No. 351 Accession No. 8015734—Abstract: JP 1203313 A.
2002 Derwent Information Ltd. Dialog File No. 351 Accession No. 11648088—Abstract EP 815839 A.
2002 Derwent Information Ltd. Dialog File No. 351 Accession No. 12265618—Abstract DE 19727504 A.
Noveon: "Pemulen TR-1 and TR-2 emulsifiers; Waterproof Sunscreen Emulsions Prepared With Pemulen Polymers" Polymers for Personal Care—Noveon, 'Online! Mar. 1995, XP002263121.

* cited by examiner

*Primary Examiner*—MP Woodward
*Assistant Examiner*—Bethany Barham

(57) ABSTRACT

A composition for retaining active ingredients in personal care compositions is described based on one or more polymers having a network structure in an oil phase in amounts from 0.01 to 10% by weight based on the total weight of the composition in the oil phase, the polymers including at least one associative agent, the composition further including at least one active component. The oil phase viscosity of each composition is at least 10 poise under a shear stress up to 1000 dynes/cm$^2$.

2 Claims, No Drawings

COMPOSITION AND PROCESS FOR RETAINING ACTIVE INGREDIENTS

CROSS REFERENCE TO RELATED PATENT APPLICATIONS

This is a non-provisional application of prior U.S. provisional application Ser. No. 60/302,577 filed Jul. 2, 2001.

The present invention relates to water resistant polymers dispersed in oil containing personal care compositions and formulations which aid the retention of active ingredients on mammalian skin for extended time periods. More particularly, the invention relates to water resistant polymer compositions having functional network structures dispersed in oil containing sunscreening compositions or cosmetic formulations which aid the retention of active ingredients at low polymer dose levels. As a result, active ingredients in such compositions remain efficacious and substantive on skin exposed to water, perspiration, high humidity and other aqueous environments.

The damaging effects of UV radiation from sunlight are well established and documented. To protect skin against the effects of prolonged exposure to sunlight, a variety of sunscreening compositions and formulations have been developed that includes so-called "active compounds", which absorb ultraviolet radiation in the form of sunlight, particularly in the ultraviolet region at wavelengths between 290 nm to 400 nm. To extend or prolong the active compound's effectiveness, it is desired that sunscreening compositions be resistant to removal from skin by water, perspiration, or high humidity, and remain substantive in the presence of such aqueous environments. Personal care compositions, including sunscreens, which are based on oil-in-water emulsions and which are used for cosmetic elegance present the user with continuing problems which are multi-fold and interrelated: effective delivery and skin coverage of a coating composition containing the active component, substantivity of the composition on a skin surface over extended periods of time, exposure to aqueous environments that cause the coating to wash off or wear off and exposure to mechanical stresses that cause the coating to rub off. The inability to effectively control one particular aspect of the problem often influences the ability to effectively control the remaining aspects. Therefore, the need for new polymer compositions that retain active ingredients at low polymer concentrations, that possess high viscosities under relatively low shear stresses related to application of the composition on skin (i.e. rubbing or spraying) and that obviate problems associated with personal care compositions and formulations applied to mammalian skin remain a primary objective relevant to the art. To be most effective, it is required that the compositions and formulations are applied to skin as a tough, continuous film. However, delivering such a film to the surface of skin is difficult, maintaining the film on skin over extended time periods has yet to be adequately addressed, and retaining the active component in the composition or formulation remains one of the most challenging aspects of the art.

A variety of water resistant or substantive sunscreening compositions are known in the art, however, many of these compositions and formulations suffer a number of disadvantages. Compositions and formulations containing film forming polymers that form a tough, continuous film on the skin can not tolerate large amounts of oil and other emollients. As a result, such compositions and formulations are prepared as alcoholic solutions, which are often irritating and drying to the skin, difficult to apply uniformly and which provide minimal moisturisation. Polymers incorporated in sunscreening compositions and formulations which are oil based and have a moisturizing effect on the skin, however, can not retain the active compound at low polymer concentrations and often lack cosmetic elegance (i.e. are greasy or unaesthetic in appearance). Moreover, the resulting compositions and formulations are not substantive when applied to mammalian skin exposed to water, perspiration, high humidity or other aqueous environments and mechanical stresses such as periodic re-application of the composition or formulation.

U.S. Pat. No. 4,172,122 discloses a water resistant sunscreening composition which includes a cosmetic oil base, at least one water insoluble ultraviolet light absorbing material which is soluble in the oil base, and a water insoluble acrylate polymer. Major requirement of the composition are: a) both the polymer and the ultraviolet light absorbing material(s) must be soluble in the oil base and insoluble in water and b) the polymer is required at levels of at least 0.5 percent by weight, based on the weight of the oil base. Repeated attempts by the inventors to prepare water insoluble acrylate polymers characterized as having a Brookfield viscosity between 12,000 and 100,000 cps. using standard solution polymerization techniques disclosed have been unsuccessful. In addition, the disclosed water insoluble acrylate polymers provide no means to entrap or retain active ingredients when combined together in an oil phase. Polymers effecting the retention of one or more active ingredients in oil containing personal care compositions and formulations at low polymer concentrations and that remain substantially resistant to aqueous environments, surfactants and mechanical stresses would, therefore, be of great utility in sunscreens, moisturizers and other personal care products.

The inventors have discovered a class of polymer compositions that are both effective in retaining active ingredients dispersed in an oil phase at low polymer concentrations and which exhibit surprisingly high oil phase viscosities under relatively low shear stresses. These polymers are prepared by polymerization of one or more monomers having low water solubilities and at least one associative agent. Incorporation of one or more associative agents provides polymers having functional network structures that retain active ingredients at low polymer concentrations when dispersed in an oil phase. Personal care compositions and formulations prepared from the water resistant, active retaining polymers remain substantive when applied to mammalian skin exposed to aqueous environments and mechanical stresses. When dispersed in an oil phase, the active retaining polymers have network structures which, effectively entrap, swell and retain active ingredients in a personal care composition and formulation. Such personal care compositions and formulations form mechanically strong, continuous films on skin. The films adhere to mammalian skin surfaces and have superior Theological properties related to their resistance to mechanical shear stresses including for example periodic re-application of the composition or formulation ("rub on"), exposure to aqueous environments ("wash off"), exposure to clothing or contact with other mammalian skin ("rub off") and movements associated with skin during mammalian motion and activities ("wear off"). The nature of the monomers used to prepare the polymers also provides a substantial waterproofing effect to skin as well as a sequestering matrix for ultraviolet absorbing, moisturizing or other types of active ingredients. In addition, the inventors have discovered that personal care compositions incorporating such polymers provide substantial waterproofing effects, as evidenced by their substantivity on mammalian skin exposed to aqueous environments, while providing dermally non-irritating, personal care formulations. Further-more, the inventors have discovered that the active retaining polymer can be dispersed in the oil base at any stage of the formulation.

A first aspect of the present invention provides a composition for retaining ingredients comprising one or more polymers having a network structure, wherein the polymer disperses in an oil phase in an amount from 0.01 to 10% by weight based on the total weight of the composition; the polymer further comprising one or more associative agents; and one or more active ingredients; the composition having an oil phase viscosity of at least 10 poise under a shear stress up to 1000 dynes/cm$^2$.

A second aspect of the present invention provides a water resistant, dermally non-irritating personal care composition comprising: (a) an effective amount of at least one active component; (b) one or more cosmetically acceptable additives; (c) a cosmetically acceptable oil phase; and (d) one or more polymers having a network structure, wherein the polymers disperse in the oil phase in an amount from 0.01 to 10% by weight based on the total weight of the composition; wherein the polymer further comprises one or more associative agents; wherein the oil phase viscosity of the composition is at least 10 poise under a shear stress up to 1000 dynes/cm$^2$. Optionally, the composition comprises of an oil-in-water emulsion.

A third aspect of the present invention provides a process for retaining an active ingredient in a composition comprising; (a) adding one or more associative agents to one or more monomers having low water solubility and polymerizing the mixture to form a polymer having a network structure; and (b) combining the polymer and one or more active ingredients in an oil phase; wherein the polymer is present in the oil phase in an amount from 0.01 to 10% by weight based on the total weight of the composition; wherein the oil phase viscosity of the composition is at least 10 poise under a shear stress up to 1000 dynes/cm$^2$. Preferably, the associative agent is added during polymerization. Alternatively, the associative agent is added after polymerization. An alternative process comprises the polymerization of one or more monomers having low water solubility, at least one monomer having one or more associative agents as functional groups reacting during polymerization to provide a polymer having a network structure. Optionally, the process comprises adding one or more reagents to the polymer after polymerization, the reagents reacting with the functional groups to provide a polymer having a network structure. Optionally, the process includes combining the polymer and one or more active ingredients in an aqueous phase.

A fourth aspect of the present invention provides a process for treating mammalian skin which comprises applying to skin one or more compositions, each composition further comprising one or more polymers having a network structure and an effective amount of one or more active ingredients in an oil phase; optionally, one or more cosmetically acceptable additives; wherein the polymer is present in the oil phase in an amount from 0.01 to 10% by weight based on the total weight of each composition, the polymer comprising one or more associative agents; wherein the oil phase viscosity of each composition is at least 10 poise under a shear stress up to 1000 dynes/cm$^2$. Preferably, the associative agent is added during polymerization. Alternatively, the associative agent is added after polymerization. An alternative process comprises the polymerization of one or more monomers having low water solubility, at least one monomer having one or more associative agents as functional groups reacting during polymerization to provide a polymer having a network structure. Optionally, the process comprises adding one or more reagents to the polymer after polymerization, the reagents reacting with the functional groups to provide a polymer having a network structure. Optionally, the process includes combining the polymer and one or more active ingredients in an aqueous phase.

A fifth aspect of the present invention provides a process for moisturising and protecting mammalian skin from ultraviolet radiation in the form of sunlight comprising applying to skin an effective amount of a sunscreen composition according to the first aspect. Alternatively, the process comprises an effective amount of a sunscreen composition according to the second aspect.

Accordingly, in a first aspect of the present invention there is provided a composition which aids in retaining one or more active ingredients present in an oil phase. The composition includes at least one polymer having a functional network structure, the polymer comprising at least one associative agent which imparts to the polymer a network structure. When dispersed with one or more active ingredients in an oil phase, the polymer effectively retains active ingredients at polymer amounts between 0.01 to 10% by weight based on the total weight of the composition. Preferably, active retaining polymers are prepared by combining one or more monomers having low or very low water solubility with at least one associative agent during polymerization of the monomers. Alternatively, the associative agent is added after polymerization of the monomers is complete. In a separate embodiment, active retaining polymers are prepared by polymerizing one or more monomers having low or very low water solubility, wherein at least one monomer further comprises one or more associative agents as functional groups in addition to an ethylenically unsaturated functional group. Optionally, the process comprises adding one or more reagents to the polymer after polymerization, the reagents reacting with the functional groups to provide a polymer having a network structure. Optionally, the process includes combining the polymer and one or more active ingredients in an aqueous phase.

As used herein, the term "water soluble" or "having water solubility" means completely soluble in water. The term "having low water solubility" means having a water solubility at 25°-50° C. of no greater than 200 millimoles/liter; the term "having very low water solubility" means having a water solubility at 25°-50° C. of no greater than 50 millimoles/liter. The term "active retaining composition" refers to a composition including one more polymers having a functional network structure which effectively retains active ingredients. The term "active retaining polymer" refers to a polymer prepared from one or more monomers having low or very low water solubility including at least one associative agent during or after polymerization to provide a polymer having a functional network structure which effectively retains active ingredients. An alternative yet equivalent meaning of the term "active retaining polymer" refers to the polymerization of one or more monomers having low or very low water solubility, wherein one or more of the monomers includes one or more types of associative agents in addition to an ethylenically unsaturated functional group or includes at least one type of functional group in addition to an ethylenically unsaturated functional group that can react as an associative agent during or after polymerization of the monomers, providing a polymer having a functional structure network structure which effectively retains active ingredients. An alternative yet equivalent meaning for the term "active retaining polymer" refers to a polymer dispersed in an oil phase that is capable of retaining one or more active ingredients, the polymer present in an amount from 0.01 to 10% by weight based on the total weight of the polymer, active(s) and ingredients, the active retaining polymer having an oil phase viscosity of at least 10 poise under a shear stress up to 1000 dynes/cm². The term "network structure" refers to a polymer structure that entraps, entangles or sequesters active components while remaining dispersed or soluble in an oil phase. This may occur via physical polymer dynamics including for example swelling, chain entrapment, chain ordering via side chains having substantial crystalline phases, large number of carbon atoms or entanglement of active components and portions of the polymer chain having hydrophobic character. An alternative meaning for the term "network structure" refers to a polymer structure resulting from chemical reactions or physical interactions of functional groups incorporated in the polymer via monomer functionalized associative agents and one or more additional reagents. The term "network structure" refers as well to the rheology of such polymers in the oil phase under relatively low shear stress as compared to polymers having no network structure, vida infra.

Monomers having low water solubility and usefully employed in the invention for preparing water resistant polymers having network structures include, but are not limited to, α,β-ethylenically unsaturated monomers. Suitable monomers include for example primary alkenes, α-olefins such as 1-butene, 1-octene, 1-decene; styrene and alkyl substituted styrenes such as α-methylstyrene and vinyltoluene; vinyl esters of $C_4$-$C_{30}$ carboxylic acids such as vinyl 2-ethylhexanoate, vinyl neodecanoate; vinyl chloride; vinylidene chloride; N-alkyl substituted (meth)acrylamides such as octylacrylamide and maleic acid amide; vinylalkyl or vinylaryl ethers with ($C_3$-$C_{30}$) alkyl groups such as stearyl vinyl ether; ($C_1$-$C_{30}$) alkyl esters of (meth)acrylic acid, such as methyl methacrylate (MMA), ethyl (meth)acrylate, butyl (meth)acrylate, 2-ethylhexyl (meth)acrylate, benzyl (meth)acrylate, lauryl (meth)acrylate, oleyl (meth)acrylate, palmityl (meth)acrylate, stearyl (meth)acrylate, cetyl (meth)acrylate, behenyl (meth)acrylate, eicosyl (meth)acrylate; blends such as cetyl-eicosyl (meth)acrylate; unsaturated vinyl esters of (meth)acrylic acid such as those derived from fatty acids and fatty alcohols; vinyl esters; vinyl ethers; vinyl amides; vinyl urethanes; olefins; cyclic anhydrides; mono and diesters of cyclic anhydrides; allyl containing monomers; multifunctional monomers such as pentaerythritol triacrylate; monomers derived from cholesterol; surfactant monomers including long chain alkoxy- or alkylphenoxy-poly(alkylene oxide) (meth)acrylates, such as $C_{18}H_{27}$-(ethylene oxide)$_{10-40}$-(meth)acrylate and $C_{12}H_{25}$-(ethylene oxide)$_{10-30}$-(meth)acrylate and the like.

Monomers having low water solubility (as referred to as hydrophobic monomers) may also contain functional groups such as for example carboxyl, hydroxy, amino, amido, aldehyde, epoxy, acetoacetoxy, cyano, cyanato, isocyanato, branched alkyl, straight chain alkyl, aromatics and substituted aromatics, discotic aromatic groups with or without carbon containing spacer groups, polyethers, groups exhibiting crystalline or liquid crystalline phases, and combinations thereof to function as associative agents. The term "water resistant" polymers refers to polymers prepared from one or more monomers having low or very low water solubility wherein the amount of such monomers, based on the total weight of monomers is between 80 to 99% by weight. An alternate meaning of the term "water resistant" polymers refers to polymers having a water solubility at 25°-50° C. of no greater than about 200 millimoles/liter. The reaction of one or more monomers with one or more associative agents or with monomers incorporating associative agents as functional groups during or after polymerization affords water resistant polymers having a network structure and having a water solubility at 25°-50° C. of no greater than 200 millimoles/liter. Moreover, terpolymers, tetrapolymers and polymers including more than four different monomers prepared according to the invention have a water solubility at 25°-50° C. of no greater than about 200 millimoles/liter.

Optional monomers having water solubility useful in the invention include, but are not limited to, α,β-monoethylenically unsaturated monomers containing acid-functionality. Suitable examples include for example monomers containing at least one carboxylic acid group such as acrylic acid (AA) and methacrylic acid (MAA), (meth)acryloxypropionic acid, itaconic acid, maleic acid or anhydride, fumaric acid, crotonic acid, monoalkyl maleates, monoalkyl fumarates, monoalkyl itaconates; acid substituted (meth)acrylates and sulfoethyl methacrylate; acid substituted (meth)acrylamides such as 2-acrylamido-2-methylpropylsulfonic acid; basic substituted (meth)acrylates and (meth)acrylamides, such as amine-substituted methacrylates including dimethylaminoethyl methacrylate, tertiary-butylaminoethyl methacrylate and dimethylaminopropyl methacrylamide and the like; acrylonitrile; (meth)acrylamide and substituted (meth)acrylamide, such as diacetone acrylamide; (meth)acrolein; methyl acrylate and the like.

Polymers usefully employed according to the invention can be prepared by conventional emulsion, solution or suspension polymerization, including those processes for example disclosed in U.S. Pat. Nos. 4,427,836; 4,469,825; 4,594,363; 4,677,003; 4,910,229; 4,920,160; 5,157,084; 5,521,266 and European Patent Nos. EP 0 267,726; EP 0 331,421 and EP 0 915,108. Emulsion polymerization is preferred. Monomers used to prepare the polymers are added in a sequential process or randomly to afford non-random or random polymers.

In a separate embodiment, polymers usefully employed in the present invention are prepared as an aqueous emulsion of polymerized monomer units, at least one monomer having low water solubility, including the steps of (1) complexing at least one monomer having low water solubility with a macromolecular organic compound having a hydrophobic cavity and (2) polymerizing in an aqueous system from about 0.1% to about 100% by weight of the monomer component, based on the total weight of the polymer, of the complexed monomer having low water solubility with from about 0% to about 99.9% by weight, based on the total weight of polymer of at least one monomer having high water solubility; as described in detail in U.S. Pat. Nos. 4,797,223; 4,404,309; 5,008,329, 5,521,266; 6,040,409 6,063,857 and European publication EP 0 989 163 A1.

Suitable macromolecular organic compounds having a hydrophobic cavity useful in the polymerization method used in the present invention include, for example, cyclodextrin and cyclodextrin derivatives; cyclic oligosaccharides having a hydrophobic cavity such as cycloinulohexose, cycloinuloheptose, and cycloinuloctose; calixarenes; and cavitands. Suitable cyclodextrin and cyclodextrin derivatives useful in the method are limited only by the solubility of the cyclodextrin and cyclodextrin derivative selected under the particular polymerization conditions. Suitable cyclodextrins useful in the method include, but are not limited to, α-cyclodextrin, β-cyclodextrin and γ-cyclodextrin as well as the methyl, triacetyl hydroxypropyl and hydroxyethyl derivatives of α-cyclodextrin, β-cyclodextrin and γ-cyclodextrin. The preferred cyclodextrin derivative is methyl-β-cyclodextrin. Suitable cyclic oligosaccharides having a hydrophobic cavity, such as cycloinulohexose, cycloinuloheptose, useful in the method are described by Takai et al., Journal of Organic Chemistry, 1994, volume 59, number 11, pages 2967-2975. Suitable calixarenes useful in the method are described in U.S. Pat. No. 4,699,966, International Patent Publication WO 89/08092 and Japanese patent publications 1988/197544 and 1989/007837. Suitable cavitands useful in the method are described in Italian application 22522 A/89 and Moran et al., Journal of the American Chemical Society, volume 184, 1982, pages 5826-5828.

A preferred process for preparing aqueous dispersions of the water resistant, active retaining polymers of the present invention includes providing one or more ethylenically unsaturated monomers having low or very low water solubility, one or more water soluble (ionic) monomers, one or more associative agents and a free radical redox initiator system under emulsion polymerization conditions. The preparation of blends of two or more water resistant polymers having network structures which retain active ingredients are also usefully employed in accordance with the present invention. The process is useful for polymerizing, in an aqueous system, solution polymers or emulsion polymers, preferably random polymers of monomers having low water solubility and network structures which could not be made without incorporating the use of organic solvents, co-monomers or high levels of surfactants to aid in solubilizing monomers having low water solubilities. The process is also useful for forming water resistant polymers having network structures by solution polymerization.

A free radical initiator is utilized in solution and emulsion polymerizations. Suitable free radical initiators include hydrogen peroxide; tert-butyl hydroperoxide; sodium, potassium, lithium and ammonium persulfate and the like. A reducing agent, such as a bisulfite, including an alkali metal metabisulfite, hydrosulfite, and hyposulfite; and sodium formaldehyde sulfoxylate or a reducing sugar such as ascorbic acid or isoascorbic acid, may be used in combination with the initiator to form a redox system. Initiators usefully employed for suspension polymerization include oil soluble peroxides, hydroperoxides and azo compounds such as AIBN. The amount of initiator may be from 0.01% by weight to about 2% by weight of the monomer charged and in a redox system, a corresponding range of 0.01% by weight to about 2% by weight of reducing agent may be used. Transition metal catalysts, such as iron and copper salts, may be used.

The polymerization temperature may be in the range of about 10° C. to 120° C. in the aqueous emulsion, suspension and solution polymerizations. In the case of the persulfate systems, the temperature is preferably in the range of 60° C. to 90° C. In the redox system, the temperature is preferably in the range of 20° C. to 70° C.

For emulsion polymers, any emulsifiers or dispersing agents optionally employed for preparing the monomer emulsions or polymer emulsions may be anionic, cationic or nonionic types. Also a mixture of any two or more types may be used. Suitable nonionic emulsifiers include, but are not limited to, ethoxylated octylphenols, ethoxylated nonylphenols, ethoxylated fatty alcohols and the like. Suitable anionic emulsifiers include, but are not limited to, sodium lauryl sulfate, sodium dodecylbenzene sulfonate, sulfated and ethoxylated derivatives of nonylphenols, octylphenols and fatty alcohols, esterified sulfosuccinates and the like. Suitable cationic emulsifiers include, but are not limited to, laurylpyridinium chlorides, cetyldimethylamine acetate, ($C_8$-$C_{18}$) alkyldimethylbenzylammonium chlorides and the like. The level of emulsifier may be from about 0.1% to about 10% by weight, based on total monomer charged.

The polymerization method is used in the present invention to form terpolymers, tetrapolymers and polymers including more than four monomers: two or more of the monomers having low water solubility, preferably affording random polymers, which heretofore could not be made without the addition of a solvent or surfactant to aid in solubilizing monomers of low or very low water solubility, also referred to as "hydrophobic monomers". "Random polymer," as used herein, refers to a polymer formed from at least two different monomers wherein the monomer units are arranged randomly not forming repeating blocks of monomer units. For an emulsion polymer, this lack of randomness and incorporation may be judged by:

(1) poor conversion of the monomer having low water solubility evidenced by monomer pooling around the stirrer shaft and the presence of monomer droplets in the final product; (2) high gel or coagulum levels; (3) the formation of large suspension polymer particles during an emulsion polymerization; (4) phase separation or creaming of monomer droplets or large suspension particles; and (5) abnormal (non-kinetic) distribution of the monomers having high water solubility and the monomers having low water solubility because of the non-uniform distribution during polymerization of the two types of monomers evidenced by multiple glass transition temperatures as measured by differential scanning calorimetry.

In an alternative embodiment, water resistant polymers formed by the polymerization method described in U.S. Pat. No. 5,521,266 and usefully employed in the invention have a random arrangement of:
(a) about 10.0% to about 99.0% by weight, based on the total weight of the polymer, of one or more monomers having low or very low water solubility;
(b) about 0.01 to 0.5% by weight, based on the total weight of the polymer, of one or more associative agents that function via a direct cross-linking reaction and are added during or after polymerization or about 20 to 90% of one or more associative agents that function via a radically induced branching or internal cross-linking or polymerization or about 0.01 to 10% of at least one monomer having one or more associative agents as functional groups in addition to the ethylenically unsaturated group that function via chemical reactions such as condensation reactions and;
(c) optionally about 0.1% to about 9.9% by weight, based on the total weight of the polymer, of at least one monomer having water solubility;

wherein the random terpolymers, tetrapolymers and polymers including more than four monomers may be formed by either solution, suspension or emulsion polymerization in water without organic solvent or a high level of surfactant.

In a separate embodiment of the present invention the water resistant active retaining polymers may be prepared by a multistage emulsion polymerization process, in which at least two stages differing in composition are polymerized in sequential fashion. Such a process usually results in the formation of at least two mutually incompatible polymer compositions, thereby resulting in the formation of at least two phases within the polymer particles. Such particles are composed of two or more phases of various geometries such as, for example, core/shell or core/sheath particles, core/shell particles with shell phases incompletely encapsulating the core, core/shell particles with a multiplicity of cores, and interpenetrating network particles. In all of these cases the majority of the surface area of the particle will be occupied by at least one outer phase and the interior of the particle will be occupied by at least one inner phase. Each of the stages of the multi-staged emulsion polymer may contain the same monomers, surfactants, chain transfer agents, etc. as disclosed herein-above for the emulsion polymer. The polymerization techniques used to prepare such multistage emulsion polymers are well known in the art such as, for example, U.S. Pat. Nos. 4,325,856; 4,654,397; and 4,814,373.

Water resistant polymers including one or more monomers having low or very low water solubility are useful in the invention where dispersibility or solubility in an oil phase is desired, such as methods of improving water resistance and film forming properties on substrates, such as mammalian skin and the like. Water resistant polymers incorporating one or more associative agents provide such polymers with network structures, which effectively retain active ingredients when dispersed in an oil phase at low polymer concentrations, namely 0.01 to 10% by weight based on the total weight of the composition.

The water resistant, active retaining polymers formed by the preferred polymerization method described above and usefully employed in the invention include:
(a) about 10.0% to about 99.99% by weight, based on the total weight of the polymer, of one or more monomers having low or very low water solubility;
(b) optionally about 0.1% to about 9.9% by weight, based on the total weight of the polymer, of at least one monomer having high water solubility; and
(c) about 0.01 to 0.5% by weight, based on the total weight of the polymer, of one or more associative agents that function via a direct cross-linking reaction and are added during or after polymerization and/or about 20 to 90% of one or more associative agents that function via a radically induced branching or internal cross-linking or polymerization or about 0.01 to 10% of at least one monomer having one or more associative agents as functional groups in addition to the ethylenically unsaturated group that function via chemical reactions such as condensation reactions; and wherein the random polymers are formed by emulsion polymerization in water with or without organic solvents or high levels of surfactant.

The active retaining polymer includes at least one associative agent, the associative agent providing a network structure to the polymer. The term "associative agent" refers to any composition that when combined with a monomer mixture during polymerization, a polymer after polymerization or any functional group incorporated in a monomer or polymer during or after polymerization that is capable of chemically modifying, changing, ordering or altering the resulting polymer structure or conformation, as compared to the resulting polymer in the absence of an associative agent, to provide a polymer having a network structure. One or more associative agents may be combined with the monomers during the polymerization process or may be added after the polymerization of monomers. Typical examples of associative agents include, but are not limited to, the following types:
(a) associative agents that function via a free radical induced direct cross-linking reaction involving two or more ethylenically unsaturated groups and that are added during polymerization of the monomer mixture. Suitable examples include allyl methacrylate (ALMA), ethylene glycol dimethacrylate (EGDMA), butylene glycol dimethacrylate (BGDMA), methylenebisacrylamide, pentaerythritol di-, tri- and tetra-acrylates, divinyl benzene, polyethylene glycol diacrylates, bisphenol A diacrylates and combinations thereof. Low levels of this associative agent are preferred, since levels greater than about 1% by weight, especially in combination with other types of associative agents (e.g. type c), based on the total weight of the polymer, tend to over cross-link the polymer network structure such that their effectiveness in retaining active ingredients markedly decreases. Preferred amounts of the associative agent range from 0.01 to 0.5% by weight, based on the total weight of the polymer.
(b) associative agents having functional groups other than an ethylenically unsaturated group that function via a chemical reaction such as for example condensation after the polymerization of the monomer mixture is complete. Suitable associative agents of this type are ethylenically unsaturated monomers having functional groups such as for example carboxyl, hydroxy, amino, amido, aldehyde, epoxy, acetoacetoxy, cyano, cyanato, isocyanato, branched alkyl, straight chain alkyl, aromatics and substituted aromatics, discotic aromatic groups with or without carbon containing spacer groups, polyethers, groups exhibiting crystalline or liquid crystalline phases, and combinations thereof. Preferred associative agents of this type include for example glycidyl methacrylate (GMA) and N-methylol acrylamide (MOA). Optionally, the functional groups can react with one or more reagents after polymerization of the monomer mixture is complete, the reagents reacting with the functional groups to provide a polymer having a network structure. Suitable reagents include for example polyols such as ethylene glycol and glycerol, polyacids such as maleic acid and succinic acid, polyamines such as ethylenediamine, alkanolamines such as ethanolamine, amino thiols such as 1-aminoethyl thiol, and amino acids such glycine and EDTA. Low levels of the associative agent are preferred, since levels greater than about 10% by weight, based on the total weight of the polymer, tend to over cross-link the polymer network structure such that their effectiveness in retaining active ingredients markedly decreases. Preferred amounts of this associative agent range from about 0.01 to 10% by weight, based on the total weight of the polymer.
(c) associative agents that function via a free radical induced reaction resulting in chain branching, branch points and internal cross-linking of the growing polymer during polymerization of the monomer mixture. Suitable examples include propyl acrylate, butyl acrylate, 2-ethylhexyl acrylate and octyl acrylate. Amounts of this associative agent range from 10% to 99% by weight, based on the total weight of the polymer. Preferred amounts of this associative agent range from about 20% to 90% by weight, based on the total weight of the polymer.
(d) associative agents consisting of any side chains incorporated in to the polymer exhibiting crystalline phases, liquid crystalline phases, or that provide significant molecular recognition and/or chemical interactions with an active ingredient. Examples include polymer side chains bearing rigid, aromatic molecules with or without spacer groups, discotic liquid crystalline groups, polyurethane groups, long chain alkyl groups ($>C_{16}$) and poly[$(C_2$-$C_4)$alkylene)]$_{20\text{-}40}$ oxide groups. Preferred amounts of this associative agent depend on the type of side group employed.

Associative agent pairs are usefully employed in the invention. An example of a preferred associative agent pair is ALMA and butyl acrylate. The total amount of the associative agent is referred to as the degree or percent of network structure in the active retaining polymer. Occasionally, one or more of the monomer units can function as an associative agent during polymerization (e.g. alkyl acrylates such as butyl acrylate). Butyl acrylate is a monomer having a functional group capable of acting as an associative agent so that it can be considered as both a monomer having low water solubility and an associative agent, by virtue of a radically initiated cross-linking reaction it undergoes during polymerization. The associative agent provides the water resistant polymers of the invention a network structure, so that they are readily dispersed, soluble or swell in natural oils, synthetic oils, emollient oils and combinations thereof and retain active compounds at very low polymer dosages or concentrations in the oil phase, based on the total weight of the oil phase. In the absence of one or more associative agents, polymers formed from the same monomers are unable to retain active ingredients in an oil base.

Preferred active retaining polymers of the present invention are polymers having the formulas I-V

| | |
|---|---|
| (A)a(B)b(C)c(Z)z | Formula I |
| (A)a(B)b(C)c(Z')z | Formula II |
| (A)a(B)b(C)c(D)d(Z)z | Formula III |
| (A)a(M)m(C)c(Z)z | Formula IV |
| (B)b(C)c(Z')z | Formula V | wherein A is a polymerized monomer unit of a water soluble monomer including (meth)acrylic acid, present in an amount a=0.5 to 10% by weight; B is a polymerized monomer unit of a monomer selected from one or more $C_4$-$C_8$ alkyl (meth) acrylates, present in an amount b=10 to 90% by weight; C is a polymerized monomer unit selected from one or more $C_1$-$C_{50}$ alkyl (meth)acrylates, present in an amount c=25 to 75% by weight; D is a polymerized monomer unit selected from one or more $C_9$-$C_{50}$ alkyl (meth)acrylates, present in an amount d=25 to 75% by weight; Z is an associative agent, present in an amount z=0.01 to 0.5% by weight if the associative agent is of type (a) or z=0.1 to 10% by weight of type (b) or z=20 to 90% by weight if type (c); Z' is a polymerized monomer unit selected from one or more $C_1$-$C_{50}$ alkyl (meth) acrylates having one or more associative agents as functional groups; and M is polymerized monomer unit which includes a blend or mixture of monomers selected from $C_1$-$C_{50}$ alkyl (meth)acrylates, present in an amount d=25 to 75% by weight. Occasionally, one or more of the monomer units can function as an associative agent during polymerization (e.g. alkyl acrylates such as butyl acrylate). "Monomer unit" refers to particular kinds of monomers (A-D, M) incorporated in the active retaining polymers. Monomers A-D and M are randomly arranged in the active retaining polymers of the invention. Water resistant, active retaining polymers having more than four monomers are also usefully employed and easily accommodated in accordance with the present invention. In a preferred embodiment, the active retaining polymers of the present invention include terpolymers, tetrapolymers, and combinations thereof.

In a preferred embodiment, the polymer comprises a) 0.1 to 5% by weight of polymerized residues of (meth)acrylic acid; b) 15 to 75% by weight B of polymerized residues of a monomer selected from one or more $C_4$-$C_8$ alkyl (meth)acrylates; c) 25 to 75% by weight of polymerized residues of a monomer selected from one or more $C_9$-$C_{50}$ alkyl (meth) acrylates; and d) 0.01 to 90% by weight of one or more associative agents.

Preferably, the active retaining polymer compositions are terpolymers, tetrapolymers or higher polymers incorporating monomer units of (meth)acrylic acid, $C_4$-$C_{50}$ alkyl (meth) acrylates, methyl (meth)acrylate, and allyl methacrylate (ALMA). The polymers are prepared from relatively high levels (80 wt. % to 99.00 wt. % based on the total polymer weight) of monomers having low or very low water solubility, relatively low levels (0.1 wt. % to 10 wt. % based on the total polymer weight) of ionic or water soluble monomers such as for example methacrylic acid or acrylic acid and at least one associative agent such as for example ALMA (0.01 wt. % to 0.5 wt. %). ALMA functions via radical induced cross-linking reaction to provide the water resistant polymer having a network structure. When amounts of this type of associative agent exceed about 0.5%, the polymer effectiveness in retaining active ingredients in an oil phase decreases substantially at low polymer levels, especially when used in combinations with other types of associative agents, such as for example type c. The terpolymer includes from 80% to 99.99% by weight of a combination of monomers having low or very low water solubility (also known as hydrophobic monomers) selected from $C_1$-$C_{50}$ alkyl (meth)acrylates and from 0.1% to 10% by weight of water soluble or ionic monomers. Preferably, the terpolymer includes from 90% to 99.99% by weight of a combination of two or more (hydrophobic) monomers having low or very water solubility selected from for example $C_1$-$C_{50}$ alkyl (meth)acrylates, from 0.1% to 10% by weight of ionizable water soluble monomers in the form of (meth) acrylic acid and from 0.01 to 1.0% by weight of at least one associative agent. More preferably, the terpolymer includes up to 98% by weight of a combination of hydrophobic monomers in the form of $C_4$-$C_{50}$ alkyl (meth)acrylates, from 1% to 3% by weight of (meth)acrylic acid and from 0.1 to 1.0% by weight of at least one associative agent.

Alkyl (meth)acrylates are monomers capable of acting as an associative agent so that it can be considered as both a monomer having low water solubility and an associative agent, by virtue of a radically initiated cross-linking reaction it undergoes during polymerization. The term "alkyl (meth) acrylate" refers to either the corresponding acrylate or methacrylate ester. Similarly, the term "(meth)acrylic" refers to either acrylic acid or methacrylic acid and its corresponding derivatives, such as esters or amides. "Ionic monomers" refer to monoethylenically unsaturated monomers which are preferably water soluble under the conditions of emulsion polymerization, as described in U.S. Pat. No. 4,880,842. "Hydrophobic monomers" refer to monoethylenically unsaturated monomers which have low or very low water solubility under the conditions of emulsion polymerization, as described in U.S. Pat. No. 5,521,266. Monomers suitable for preparing the active retaining polymer compositions and its use in the processes of the present invention are hydrophobic and ionizable water soluble monoethylenically unsaturated monomers which can be subjected to free radical polymerization in a straight forward manner using standard emulsion polymerization techniques. The advantages of the water resistant active retaining polymers and its use in personal care composition, formulations and associated processes of the invention are achieved when the polymer composition includes relatively large amounts of monomers having low or very low water solubility compared to amounts of water soluble (ionic) monomers and include at least one associative agent or at least one monomer having a functional group that includes an associative agent in addition to the ethylenically unsaturated functional group. Active retaining polymers prepared in by both methods are random polymers having a functional network structure.

In a separate embodiment, the polymer is prepared from a blend of aqueous emulsion polymers comprising from 1% to 5% by weight of at least one ionic monomer and from 95% to 99% of two or more monomers having low water solubility, and one or more associative agents.

Active retaining polymers usefully employed in accordance with present invention are combined with at least one active component in an oil phase or combined with other dermally non-irritating additives and formulated in an oil phase or an aqueous phase. The rheological or flow properties of the active retaining polymer and the active component in the oil phase are important. For example, the active retaining polymer in an oil based composition or oil based formulation should be effective in retaining the active component in an amount from 0.01 to 10% by polymer weight based on the total weight of the composition or formulation in the oil phase. In a preferred embodiment, the amount of active retaining polymer is present in the oil phase in an amount from 0.01 to 5% by weight. In the most preferred embodiment, the active retaining polymer is present in the oil phase in an amount between 0.01 and 1%.

The active retaining polymer compositions or formulations in an oil phase exhibit significantly high viscosities (table II); oil phase viscosities of 10 poise or greater, under relatively low shear stresses, shear stresses ranging from 2.5 to 1000 dynes/cm$^2$. Oil phase viscosity ranges from 10 poise to 100,000 poise for the active retaining polymer compositions or formulations under shear stresses ranging from 2.5 to 1000 dynes/cm$^2$. Oil phase viscosities for polymer compositions or formulations of the present invention are unexpectedly large as compared to the same rheological values for oil bases including for example neat oils, emollient oils with actives, polymers in oil bases, or acrylic based polymers combined with active ingredients in oil bases or formulated in to sunscreens or moisturizers, including polymers and formulations for example disclosed in U.S. Pat. Nos. 5,736,125; 5,288,493; 5,219,558; 4,552,755 and 4,172,122. The latter polymer compositions or formulations exhibit markedly lower viscosities; oil phase viscosities lower than 10 poise under the same shear stress, shear stresses ranging from 2.5 to 1000 dynes/cm$^2$ (Table VII). Under shear stresses of greater than 1000 dynes/cm$^2$, the active retaining polymer compositions or formulations of the present invention exhibit "shear thinning". Shear thinning means that as the polymer compositions or formulations are subjected to increasing shear, viscosity markedly decreases. Even under high shear stresses, however, the viscosities of the active retaining polymer compositions or formulations in the oil phase are still significantly higher as compared to oil bases including neat oils, emollient oils with actives, polymers in oil bases, or acrylic based polymers combined with active ingredients in oil bases or formulated in to sunscreens or moisturizers, including polymers and formulations for example disclosed in U.S. Pat. Nos. 5,736,125; 5,288,493; 5,219,558; 4,552, 755 and 4,172,122.

The rheological values of active retaining polymer compositions and formulations in the oil phase were measured using a standard stress rheometer having a small cone angle. Details of the stress rheometer Theological measurements, and interpretation of Theological values are described by Christopher W. Macosko in "Rheology: Principles, Measurements and Applications, VCH Publishers: New York, 1994; the contents of which are usefully employed in the present invention. Shear stress sweep measurements were performed on active retaining oil based polymer compositions and formulations for comparison with emollient oils, emollient oils with actives, polymers in oil bases, or acrylic based polymers combined with active ingredients in oil bases or formulated in to sunscreens or moisturisers, including polymers and formulations described above. Oil phase viscosity data and shear stress data are summarised for representative active retaining polymer compositions and formulations of the present invention as Examples along with comparative examples. Viscosity data were measured for samples under shear stress levels generated such that the shear stresses are logarithmically incremented, resulting in equally spaced data points when viscosities are plotted as a function of the logarithmically scaled shear stresses. Shear stress sweep measurements were conducted over five decades of shear stress from 2.5 to 10,000 dynes/cm$^2$.

The active retaining polymer compositions of the present invention are emulsion polymers (latexes) having an average particle diameter that ranges from 20 nm to 1,000 nm, preferably from 100 nm to 600 nm. Particle sizes herein are those determined using a Brookhaven Model BI-90 particle sizer manufactured by Brookhaven Instruments Corporation, Holtsville N.Y., and polymer particle diameters are reported as "effective diameter". Also contemplated are multimodal particle size active retaining emulsion polymers wherein two or more distinct particle sizes of or very broad distributions are provided as described in U.S. Pat. Nos. 5,340,858; 5,350,787; 5,352,720; 4,539,361 and 4,456,726. In addition, active retaining suspension polymers with particle sizes greater than 1000 nm are contemplated.

The active retaining polymer compositions of the present invention may be used as prepared (in slightly acidic form) or the acidic groups (~1 to 3%) may be neutralised to form salts containing carboxylate anions. Preferred alkali metal ions typically include sodium or potassium, alkaline earth metal cations such as magnesium and calcium, ammonium or tetra-alkylammonium salts, such as tetramethylammonium, or organic amine salts, such as the salts of tri-$C_1$-$C_4$ alkylamines, hydroxyethylamines, mono-$C_1$-$C_4$ alkanolamines, di-$C_1$-$C_4$ alkanolamines and tri-$C_1$-$C_4$ alkanolamines, and mixtures thereof.

The invention provides active retaining polymers, personal care compositions and formulations including any cosmetically acceptable oil base. A suitable oil base includes any oil or mixture of oils which are conventionally used in the personal care products. Examples include saturated fatty esters and diesters, such as isopropyl palmitate, octyl palmitate, butyl stearate, isocetyl stearate, octadodecyl stearoyl stearate, diisopropyl adipate, dioctyl sebacate, paraffin oils, paraffin waxes, animal oils and vegetable oils such as mink oil, coconut oil, soybean oil, palm oil, corn oil, cocoa butter, sesame oil, lanolin oil, fatty alcohols such as stearyl alcohol, isostearyl alcohol, isocetyl alcohol. The oils listed are merely examples are not intended to limit the invention in any way. In general, any hydrophobic material or mixtures thereof which are toxicologically safe for human or animal use may constitute the oil base of the present invention.

The personal care compositions and formulations containing the active retaining polymers are of four basic compositions: oil dispersions, oil-in-water emulsions, water-in-oil emulsions and solutions from one or more organic solvents. The oil dispersions are prepared by dispersing the active retaining polymers in the oil base with one or more active ingredients. The active retaining polymers can be dispersed in an oil phase or are prepared as an aqueous suspension prior to preparing the final oil-in-water or water-in-oil emulsion. The polymers can be added in either phase at any stage in preparing the composition or formulation. Personal care formulations are prepared by combining the active retaining polymer, an oil base, optionally including an aqueous phase, one or more active ingredients and optional additives by warming the mixture with slow agitation. The oil based personal care compositions and formulations include from 0.01 to 10% by weight of at least one active retaining polymer based on the total weight of the formulation. The cosmetically acceptable base of the compositions and formulations may be solid or liquid, but the entire formulation is preferably fluid at skin temperatures for ease of application. Suitable solvents for preparing a solution of the polymer are typically those used in the art and include alcohols such as ethyl alcohol and volatile silicones such as cyclomethicone. Suitable additives include fragrances, fillers, dyes, colorants, preservatives, biocides, antioxidants, other such additives conventionally used in personal care products without negatively impacting substantivity and combinations thereof.

The invention provides dermally applied personal care compositions and formulations including active retaining polymers dispersed in an oil base and one or more active ingredients. Suitable active ingredients include but are not limited to sunscreening actives, moisturising actives such as moisturizing oils, cleansing actives for personal care, detergent actives for personal care, vitamins, folic acid derivatives, exfoliating agents, deodorising actives, fragrance actives, skin exfoliating actives, topical medicament actives for personal care, cosmetic agents for personal care, hair conditioners, facial care products, body washes, topical preparations, infrared (IR)-absorbing materials for personal care, acne medications and combinations thereof. Cosmetic agents include for example mascaras, eyeliners, lipsticks, powders, paints, foundations and masks.

Suitable sunscreen actives include inorganic oxides such as ultra fine titanium dioxide and zinc oxide, cinoxate(2-ethoxy-ethyl-p-methoxy-cinnamate); diethanolamine-p-methoxy-cinnamate; digalloyl trioleate ethyl 4-bis(hydroxypropyl) aminobenzoate; ethylhexyl-p-methoxy-cinnamate; 2-ethylhexyl salicylate; glyceryl aminobenzoate; homosalate (3,3,5-trimethylcyclohexyl salicylate); triethanolamine salicylate; 2-phenyl-benzimidazole-5-sulfonic acid; sulisobenzone(2-hydroxy-4-methoxy-benzophenone-5-sulfonic acid); Padimate A (amyl p-dimethylaminobenzoate); Padimate O (octyl dimethyl para aminobenzoate); and menthyl anthranilate, Sun-spheres® and mixtures thereof.

The sunscreening compositions and formulations also may include a sunscreen material particularly suitable for ultraviolet-A (320-400 nm) protection. This compound suitably is selected from oxybenzone, dioxybenzone; 2-ethylhexyl-2-cyano-3,3 diphenylacrylate; methyl benzilidine camphor; 4-t-butyl-4'-methoxydibenzoyl-methane and mixtures thereof.

Sunscreen compositions and formulations of the invention may be formed using conventional emulsion techniques and inexpensive agitation equipment. The sunscreen compositions and formulations thus formed are stable emulsions, the polymers effectively retaining active ingredients at low polymer concentrations, ranging from 0.01 to 10% by polymer weight based on the total weight of the composition in the oil phase; the formulation having an oil phase viscosity of at least 10 poise under a shear stress up to 1000 dynes/cm$^2$. It is preferred that the formulation consists of an oil-in-water emulsion.

When applied to mammalian skin, these personal care compositions and formulations of the present invention form an oil film on the skin surface. This film gives the skin a moist, glossy appearance which provides cosmetic elegance.

The films helps protect the skin from the drying, oxidizing effects of the environment, and the ultraviolet light-absorber protects the skin from the damaging rays of the sun. The polymer retains the ultraviolet light-absorber onto the skin so that a significantly greater percentage of sunscreen protection is provided at lower polymer concentrations after than with compositions not containing one or more active retaining polymers. Moreover the compositions and formulations remain substantive for extended periods of time and prolonged exposure to aqueous environments such as water, humidity or perspiration.

Oil-in-water emulsions are generally prepared by heating the oil and water phases, and slowly adding the water phase to the oil phase with good agitation. Homogenization may be helpful, but it is not necessary. The addition of low levels of stabilizing ingredients in the water phase has been shown to be helpful. Salts such as magnesium sulfate have proven to be useful emulsion stabilizers, and they do not significantly affect the water resistance of the formulations. The addition of water soluble gums such as guar derivatives, xanthan gum, and aloe vera and thickeners such as hydroxyethyl cellulose, hydroxymethyl cellulose and carboxyvinyl polymers have been found to be helpful in stabilizing the emulsions.

The personal care compositions and formulations are usefully employed in accordance with the present invention as creams, lotions, gels, towelettes, wipes, masks, adhesive pads, sprays delivered from solvent and any conventional means used in personal care art.

The following examples illustrate specific aspects and particular embodiments of the invention which, however, are not to be construed as limited thereby.

The following abbreviations are used in the examples:

| | |
|---|---|
| BA | butyl acrylate |
| MMA | methyl methacrylate |
| MAA | methacrylic acid |
| AA | acrylic acid |
| SMA | stearyl methacrylate |
| CEMA | cetyl-eicosyl methacrylate |
| ALMA | allyl methacrylate |
| g | grams |
| nm | nanometers |
| OP | octyl palmitate |
| IOA | isooctyl acrylate |
| IPP | isopropyl palmitate |

Water Resistant, Active Retaining Polymer Compositions

EXAMPLES 1-8

A standard emulsion polymerization method was used to prepare examples 1-8 and comparative examples. The emulsion polymerizations were carried out in a 4-liter round bottom flask with four necks equipped with a mechanical stirrer, temperature control device, condenser, monomer and initiator feed lines and a nitrogen inlet. The monomer emulsion and initiator solutions were fed over a period of three hours maintaining the temperature at 85° C.

Table I summarizes typical water resistant, active retaining polymer compositions usefully employed in accordance with the present invention.

TABLE I

Water Resistant, Active Retaining Polymer Compositions

| Example # | Composition (by weight %) |
|---|---|
| 1 | 40SMA/20BA/39MMA/1MAA |
| 2 | 31CEMA/49BA/19MMA/1MAA |
| 3 | 31CEMA/49BA/18.98MMA/1MAA/0.02ALMA |
| 4 | 31CEMA/49BA/19MMA/1AA |
| 5 | 31CEMA/31BA/36.6MMA/1.4MAA |
| 6 | 31CEMA/49BA/18.6MMA/1.4MAA |
| 7 | 40SMA/20BA/38.95MMA/1MAA/0.05ALMA |
| 8 | 70BA/28MMA/1.5MAA/0.1ALMA |
| 9 | None |

Characterization of Water Resistant, Active Retaining Emulsion Polymers

Several techniques were used to determine whether the monomers having very low water solubility of Examples 1-8 were incorporated randomly into the final polymer. First, lack of pooling of monomer having very low water solubility around the stirring vortex was evidence of good conversion of the monomer having very low water solubility into the final polymer. Second, lack of large 1-10 microns particles and monomer droplets, collected (as is or by centrifugation or from creamy layer) and characterized by optical microscopy, was evidence of good incorporation of the monomer having very low water solubility into the final polymer. Third, lack of formation of gel (collected through a 100 mesh screen) was evidence that the polymerization generally ran well. Finally, a single glass transition temperature at approximately the calculated copolymer values using literature data, as measured by differential scanning calorimetry at a heating rate of 20° C./minute, was evidence of good incorporation of the monomer having very low water solubility to form a random copolymer.

Preparation of Oil Phase Used for Oil Phase Rheology Measurements of Water Resistant, Active Retaining Polymers An oil phase containing 0.5 g of a water resistant, active retaining polymer (freeze dried) and the following additives:
7.5 g Octyl Methoxycinnamate (OMC)
3.0 g Benzophenone-3
3.0 g Octyl Salicylate
6.0 g Octyl Palmitate were combined with stirring and heated to 70-75° C. until the polymer had completely swelled into the oil phase. The time required for swelling the polymer in to the oil phase depended on the amount and particle size of the freeze dried polymer used. Small polymer particles were made by grinding freeze dried polymer prior to addition to the oil phase.

The maximum viscosity for each water resistant, active retaining polymer of the current invention from the above plot is summarized in Table II.

TABLE II

Maximum Oil Phase Viscosities of Water Resistant, Active Retaining Polymer Compositions (including control)

| Example # | Viscosity, P |
|---|---|
| 1 | 9400 |
| 2 | 3100 |
| 3 | 11000 |
| 4 | 8100 |
| 5 | 990 |
| 6 | 1040 |
| 7 | 27 |
| 8 | 12 |
| 9* | 0.27 |

*control

As shown in Table II, all of the water resistant, active retaining polymers of the current invention have a maximum viscosity of greater than 10 poise under a shear stress up to 1000 dynes/cm$^2$.

Sunscreen Formulations

Two sunscreen formulations were used to test the effective water resistance for the water resistant, active retaining polymer compositions of the current invention and to compare their performance to materials outside of this invention including some commercial products. These formulations are of the oil-in-water emulsion type stabilized with non-ionic emulsifiers. Formulation Type I was targeted to have an effective SPF of 15, and formulation Type II an SPF of 35:

TABLE III

Sunscreen Formulations

| Ingredient | Weight % |
|---|---|
| Formulation Type I | |
| Phase A | |
| Deionized Water | 65.00 |
| Hexylene Glycol | 2.00 |
| Carbomer | 0.20 |
| Phase B | |
| Escalol ® 557 (ISP) | 7.50 |
| Escalol ® 567 (ISP) | 3.00 |
| Escalol ® 587 (ISP) | 3.00 |
| Ceraphyl ® 368 (ISP) | 6.00 |
| Cerasynt ® 840 (ISP) | 2.00 |
| Cerasynt ® 945 (ISP) | 5.00 |
| Phase C | |
| Deionized Water | 5.00 |
| Triethanolamine 99% | 0.20 |
| Phase D | |
| Germall ® Plus (ISP) | 0.60 |
| LiquaPar ® Optima (ISP) | 0.50 |
| Total | 100.00 |
| Formulation Type II | |
| Phase A | |
| Deionized Water | 54.60 |
| Hexylene Glycol | 2.00 |
| Carbomer | 0.15 |
| Phase B | |
| Escalol ® 557 (ISP) | 7.50 |
| Escalol ® 567 (ISP) | 7.50 |
| Escalol ® 587 (ISP) | 5.00 |
| Escalol ® 597 (ISP) | 10.00 |
| Cerasynt ® 840 (ISP) | 2.00 |
| Cerasynt ® 945 (ISP) | 5.00 |
| Phase C | |
| Deionized Water | 5.00 |
| Triethanolamine 99% | 0.15 |
| Phase D | |
| Germall ® Plus (ISP) | 0.60 |
| LiquaPar ® Optima (ISP) | 0.50 |
| Total | 100.00 |

Escalol ®, Ceraphyl ®, Cerasynt ®, Germall ® Plus and Liquapar ® are registered trademarks of ISP Corporation.

Formulations were made using the following procedure: Water and Hexylene Glycol of Phase A were combined at room temperature. Carbomer was slowly sprinkled onto the surface while stirring. After incorporating all the carbomer, Phase A was heated to 70-75° C. with stirring. Phase B was combined, heated to 75-80° C. and stirred until uniform. Phase B was slowly added to Phase A with homogenization at 70° C. When batch appeared uniform, Phase C was added with homogenization. After batch appeared uniform, heat was turned off and mixing was switched to sweep at 60° C. Continued to sweep throughout cool-down. Phase D added with stirring at 45° C. Water was added to make up for loss during heating and stirred to room temperature.

Examples and Water Resistance Testing Results

Following non-limited examples were prepared based on two previously described sunscreen formulations. The water resistant, active retaining polymer compositions of the current invention were added into the formulations during the stage 4 of described procedure (during cool-down at 45° C. with stirring) prior to addition of preservatives (Phase D). Commercial products that were used for comparison purposes were added into the Phase B. The order of addition has no effect on the performance of the water resistant, active retaining polymer compositions of the current invention.

Water Resistance Test Method

The water resistance of sunscreen formulations was determined by measuring the amount of UV light absorbed by sunscreen active components before and after immersion in water. Formulations were applied onto the artificial skin (Vitro-Skin™, IMS Inc. Millford, Conn.) and the UV absorbance was measured spectrophotometrically. The in-vitro water resistance tests were conducted as follows:

a) 6-7 mg of formulation were applied on pre-hydrated (24 hours at room temperature and 90-95% relative humidity) pieces of Vitro-Skin™ (28×38 mm) that were mounted in 35 mm slide mounts;
b) The emulsion was carefully spread using a rubber-gloved finger with initial circular and then linear motion. Samples were left in the humidity chamber (room temperature and 90-95% relative humidity) for 20 minutes to allow for emulsion coalescence;
c) Four (4) UV spectra were collected (Carry 1-E UV-Vis Spectrophotometer) for each sample in the range of 250-350 nm with a 90° rotation before each scan. Absorbance readings were taken for 310 and 290-292 nm and were labeled as the initial absorbance—($A_i$);
d) Samples were immersed in temperature controlled water bath (25±0.2° C.) for 80 minutes with constant mixing (paddle type impeller at 50 rpm). The volume of water bath was large enough (2000 ml) to prevent high concentration of sunscreen in solution and possibility of re-adsorption;
e) After immersion, samples were taken out of water, lightly shaken to remove the largest water droplets and hung in the air (room temp., ~50% relative humidity) for 30 minutes for initial drying. Then, the samples were placed in the humidity chamber for 120 minutes;
f) Final absorbance readings—($A_f$) were taken in the same manner as the initial ones, and the % water resistance was calculated as:

% water resistance=$A_f/A_i \times 100$

Samples were run in quadruplicates and the blank control sample (without sunscreen) was treated and measured in exactly the same way. The control sample was immersed in the separate water bath to prevent sunscreen adsorption from solution.

TABLE IV

Water Resistance Testing Results for Formulation Type 1. All examples used at 0.5 wt %

| Example Number | % Water Resistance |
|---|---|
| 1 | 95.8 ± 5.2 |
| 2 | 96.3 ± 3.9 |
| 3 | 92.6 ± 5.8 |
| 4 | 91.5 ± 4.4 |
| 5 | 91.7 ± 9.6 |
| 6 | 97.8 ± 3.1 |
| 7 | 93.8 ± 5.3 |
| 8 | 88.8 ± 6.3 |
| 9* | 51.2 ± 8.3 |

*control

As shown in Table IV, the water resistant, active retaining polymer compositions of the current invention, that have a maximum viscosity of greater than 10 poise under a shear stress up to 1000 dynes/cm², are very effective at very low amounts (0.5 wt %) compared to the control in Formulation Type 1 that is a typical medium SPF formulation.

TABLE V

Water Resistance Testing Results for Formulation Type 2. All examples used at 1.0 wt %

| Example Number | % Water Resistance |
|---|---|
| 1 | 99.1 ± 2.7 |
| 2 | 100.0 ± 5.0 |
| 6 | 100.0 ± 4.0 |
| 8 | 100.0 ± 5.0 |
| 9* | 20.0 ± 4.4 |

*control

Surprisingly, Table V shows that the water resistant, active retaining polymer compositions of the current invention are completely effective at low amounts (1.0 wt %) in Formulation Type 2. This formulation is a typical high SPF formulation that is very hard to retain on skin, as shown by the baseline water resistance of 20%.

The following non-limited examples were prepared to assess the dose response for the active retaining polymers of the current invention.

TABLE VI

Water Resistance Testing Results for Formulation Type 1 as a function of concentration.

| Example Number | Amount (wt %) | % Water Resistance |
|---|---|---|
| 6 | 0.2 | 73.9 ± 9.0 |
| 6 | 0.5 | 97.8 ± 3.1 |
| 6 | 1.0 | 98.8 ± 2.1 |
| 8 | 0.2 | 66.7 ± 9.6 |
| 8 | 0.5 | 88.8 ± 6.3 |
| 8 | 1.0 | 94.6 ± 7.0 |
| 9 | 0 | 51.2 ± 8.3 |

As shown in Table VI, the water resistant, active retaining polymer compositions of the current invention are better than baseline at extremely low amounts (0.2 wt %). At 1.0 wt % virtually complete retention is observed using Formulation Type 1 that is a typical medium SPF formulation.

COMPARATIVE EXAMPLES

TABLE VII

Maximum Oil Phase Viscosity for Polymer Examples 10–14.

| Example Number | Viscosity, P | Composition (by weight %) |
|---|---|---|
| 9 | 0.27 | None |
| 10 | 0.41 | 90 IOA/10 AA in OP |
| 11 | 1.2 | 40SMA/20BA/39MMA/1MAA in OP |
| 12 | 0.73 | 40SMA/20BA/39MMA/1MAA in OP |
| 13 | 0.7 | 31CEMA/49BA/19MMA/1MAA |
| 14 | 4.9 | 31CEMA/49BA/18.8MMA/1MAA/0.2ALMA |

Table VII shows that all of these polymers have a maximum viscosity significantly below 10 P and therefore do not meet the criteria for the water resistant, active retaining polymers of the current invention. Example 9 is a control. Example 10 was prepared according to the solution polymerization procedure disclosed in Kubik et al (U.S. Pat. No. 4,172,122). The molecular weight of the polymer is low and the viscosity measured is only within the extremely low viscosity range claimed (50 cps.). The low viscosity indicates no network structure is present in the polymer. Examples 11 and 12 were also prepared in solution and the reaction conditions do not allow a network structure to form resulting in very low molecular weight acrylic polymers. In Example 13 a chain transfer agent, n-dodecyl mercaptan has been added to prevent the formation of a network structure necessary for retaining active ingredients. Example 14 exemplifies a situation where too large an amount of the associative agents (BA and ALMA) are added. High levels of associative agents tend to over cross-link the polymer network structure such that their effectiveness in retaining active ingredients markedly decreases.

TABLE VIII

Water Resistance Testing Results for Formulation Type 1, All examples used at 1.0 wt %

| Example Number | % Water Resistance |
|---|---|
| 9 | 51.2 ± 8.3 |
| 10 | 64.2 ± 8.5 |
| 11 | 35.9 ± 12.1 |
| 12 | 21.6 ± 7.4 |
| 13 | 48.2 ± 9.2 |
| 14 | 71.7 ± 11.9 |

As shown in Table VIII, polymer examples 10-14 do not perform nearly as well as the water resistant, active retaining polymer compositions of the current invention (compare to Table IV) even when used at twice the amount of polymer. Examples 11 and 12 are significantly worse than the no polymer control. Since none of these polymers had a maximum viscosity greater than 10 poise under a shear stress up to 1000 dynes/cm$^2$, they help define the viscosity requirement for water resistant, active retaining polymer compositions of the current invention.

The inventors repeated many of the examples given in U.S. Pat. No. 4,172,122 using the solution polymerization method disclosed and were unable to obtain Brookfield viscosities between 12,000 and 100,000 cps. for the examples disclosed.

We claim:

1. A process for retaining an active ingredient in a composition comprising: (a) polymerizing butyl acrylate, methacrylic acid, methyl methacrylate and cetyl-eicosyl methacrylate by aqueous emulsion polymerization to form a polymer having a network structure of 1.4% by weight of polymerized residues of methacrylic acid, 49% by weight of polymerized residues of butyl acrylate, 18.6% by weight of polymerized residues of methyl methacrylate and 31% by weight of polymerized residues of cetyl-eicosyl methacrylate and (b) combining the polymer and one or more active ingredients in an oil phase; wherein the polymer is present in the oil phase in an amount from 0.01 to 10% by weight based on the total weight of the composition.

2. The process of claim 1 in which said one or more active ingredients are selected from the group consisting of sunscreening actives, moisturizing actives, vitamins, folic acid derivatives, exfoliating agents, deodorizing actives, fragrances, cosmetic agents for personal care, hair conditioners, infrared (IR)-absorbing materials for personal care, acne medications and combinations thereof.

* * * * *